(12) United States Patent
Keyvani

(10) Patent No.: US 10,829,425 B2
(45) Date of Patent: Nov. 10, 2020

(54) METHODS AND APPARATUSES FOR PURIFYING CRUDE PROPANE

(71) Applicant: Lyondell Chemical Technology, L.P., Houston, TX (US)

(72) Inventor: Majid Keyvani, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/823,006

(22) Filed: Mar. 18, 2020

(65) Prior Publication Data

US 2020/0216375 A1    Jul. 9, 2020

Related U.S. Application Data

(62) Division of application No. 16/393,359, filed on Apr. 24, 2019, now Pat. No. 10,640,437.

(Continued)

(51) Int. Cl.
| | | |
|---|---|---|
| *B01J 20/18* | (2006.01) | |
| *C07C 7/13* | (2006.01) | |
| *B01J 29/70* | (2006.01) | |
| *C07C 9/08* | (2006.01) | |
| B01D 53/14 | (2006.01) | |
| C07C 27/26 | (2006.01) | |
| C07C 47/06 | (2006.01) | |
| C07D 301/32 | (2006.01) | |
| C07D 303/04 | (2006.01) | |

(52) U.S. Cl.
CPC .............. *C07C 7/13* (2013.01); *B01J 20/18* (2013.01); *B01J 29/7007* (2013.01); *C07C 9/08* (2013.01); B01D 53/1487 (2013.01); C07C 27/26 (2013.01); C07C 47/06 (2013.01); C07D 301/32 (2013.01); C07D 303/04 (2013.01)

(58) Field of Classification Search
CPC .. C07C 7/13; C07C 9/08; C07C 27/26; C07C 47/06; C07C 301/32; C07C 303/04; C07C 7/005; C07C 7/20; C07C 7/148; B01J 20/18; B01J 29/7007; B01D 53/1487
USPC ........ 585/802, 820, 823, 824, 860; 422/255, 422/262, 608, 611
See application file for complete search history.

(56) References Cited

U.S. PATENT DOCUMENTS

| | | |
|---|---|---|
| 5,160,425 A | 11/1992 | Lewis |
| 5,582,808 A | 12/1996 | Patek |

(Continued)

FOREIGN PATENT DOCUMENTS

| | | |
|---|---|---|
| EP | 2177514 A1 | 4/2010 |
| WO | 2011118823 A1 | 9/2011 |

OTHER PUBLICATIONS

International Search Report and Written Opinion dated Aug. 23, 2019 (Aug. 23, 2019) for Corresponding PCT/US2019/028915.

*Primary Examiner* — Thuan D Dang

(57) ABSTRACT

Systems and methods for purifying crude propane streams are provided herein. For example, in some embodiments, methods are provided including passing a crude propane stream to a fixed bed reactor containing a Beta zeolite configured to reduce the propylene oxide content of the crude propane stream and produce a propylene-treated stream and contacting the propylene-treated stream with an acetaldehyde scavenger to produce a treated propane stream. In some embodiments, methods are provided including passing a crude propane stream through a water wash system to provide a treated propane stream having a lower propylene oxide content, a lower acetaldehyde content, or both.

3 Claims, 5 Drawing Sheets

Related U.S. Application Data

(60) Provisional application No. 62/662,567, filed on Apr. 25, 2018.

(56) References Cited

U.S. PATENT DOCUMENTS

| | | |
|---|---|---|
| 7,279,145 B2 | 10/2007 | Balan |
| 8,710,274 B2 | 4/2014 | Pourreau et al. |
| 2010/0197947 A1 | 8/2010 | Narahara et al. |

METHODS AND APPARATUSES FOR PURIFYING CRUDE PROPANE

CROSS-REFERENCE TO RELATED APPLICATIONS

This application is a divisional patent application of U.S. patent application Ser. No. 16/393,359, filed on Apr. 24, 2019, which claims benefit and priority of U.S. Provisional Patent Application No. 62/662,567 filed on Apr. 25, 2018, the disclosures of which are incorporated herein by reference in their entirety.

FIELD OF THE DISCLOSURE

This disclosure relates to systems and methods of purifying crude propane, including removing oxidation products from a crude propane stream

BACKGROUND

One use of propylene is in the propylene oxide/styrene monomer (POSM) manufacturing process. The POSM process contacts propylene and ethyl benzene under oxidative conditions to produce propylene oxide and styrene monomer. By-product propane is generated off the C3 splitter, however the propane can be contaminated with oxidation by-products such as acetaldehyde and propylene oxide.

Various systems and methods exist for purifying crude propane streams. For example, crude propane streams may be purified by distillation, which can be a very effective means of separation. However, distillation can be quite costly, and the separation of certain impurities from crude propane by distillation is not feasible or practical. As a result, in some circumstances, these crude propane streams are merely burned as fuel to power and/or heat other processes as they are not sufficiently pure to be used in other processes.

Accordingly, there is a continuing need for improved methods of purifying crude propane streams, including the removal of oxidation by-products from crude propane streams.

SUMMARY

In one aspect, methods of purifying crude propane streams are provided in the present disclosure. In an embodiment for example, this disclosure provides a method of purifying a crude propane stream which can comprise: providing a crude propane stream comprising propane, propylene oxide, acetaldehyde, and propylene; contacting the crude propane stream with a Beta zeolite catalyst and an aldehyde scavenger under conditions sufficient to reduce the propylene oxide content and the aldehyde content of the crude propane stream and produce a first treated propane stream. In this and other aspects, the crude propane stream can comprise propane and any one or more than one of propylene oxide, acetaldehyde, and propylene.

In other embodiments, this disclosure provides a method of purifying a crude propane stream which can comprise: providing a crude propane stream comprising propane, propylene oxide, acetaldehyde, and propylene; and passing the crude propane stream through a water wash system to provide a treated propane stream having a lower propylene oxide content, a lower acetaldehyde content, or both; wherein the water wash system comprises treating water in a water wash column with at least 15 theoretical stages. In this aspect, the crude propane stream can comprise propane and any one or more than one of propylene oxide, acetaldehyde, and propylene.

In another aspect, systems and apparatuses for purifying a crude propane stream are provided. In one embodiment, a reactor for purifying a crude propane stream is provided, in which the reactor can comprise: a fixed bed reactor having a crude propane stream inlet, the crude propane stream comprising propane, propylene oxide, acetaldehyde, and propylene; the fixed bed reactor comprising a Beta zeolite configured to contact the crude propane stream, reduce the propylene oxide content of the crude propane stream, and produce a first treated propane stream; and an acetaldehyde scavenger system configured to contact one or more of the crude propane stream and the first treated propane stream with one or more aldehyde scavengers under conditions sufficient to reduce the acetaldehyde content of the one or more of the crude propane stream and the first treated propane stream.

In another embodiment, a propane production system is provided which can comprise: a first system configured to produce a first hydrocarbon stream comprising C3 hydrocarbons; a distillation column configured to separate propylene and propane and produce a crude propane stream; and the reactor described above configured to purify the crude propane stream.

In another embodiment, a propane production system is provided in this disclosure which can include: a reboiler configured to produce a water vapor stream; a condenser configured to condense a portion of the water vapor stream to form a liquid water stream; a water wash system configured to purify a crude propane stream by washing with the liquid water stream to produce a water purge stream and a purified propane stream.

These and other aspects and embodiments are provided in the detailed description and appended claims, and certain embodiments are illustrated in the figures.

BRIEF DESCRIPTION OF THE DRAWINGS

The following figures illustrate embodiments of the subject matter disclosed herein. The claimed subject matter may be understood by reference to the following description taken in conjunction with the accompanying figures, in which like reference numerals identify like elements, and in which:

DETAILED DESCRIPTION

Figure 1:
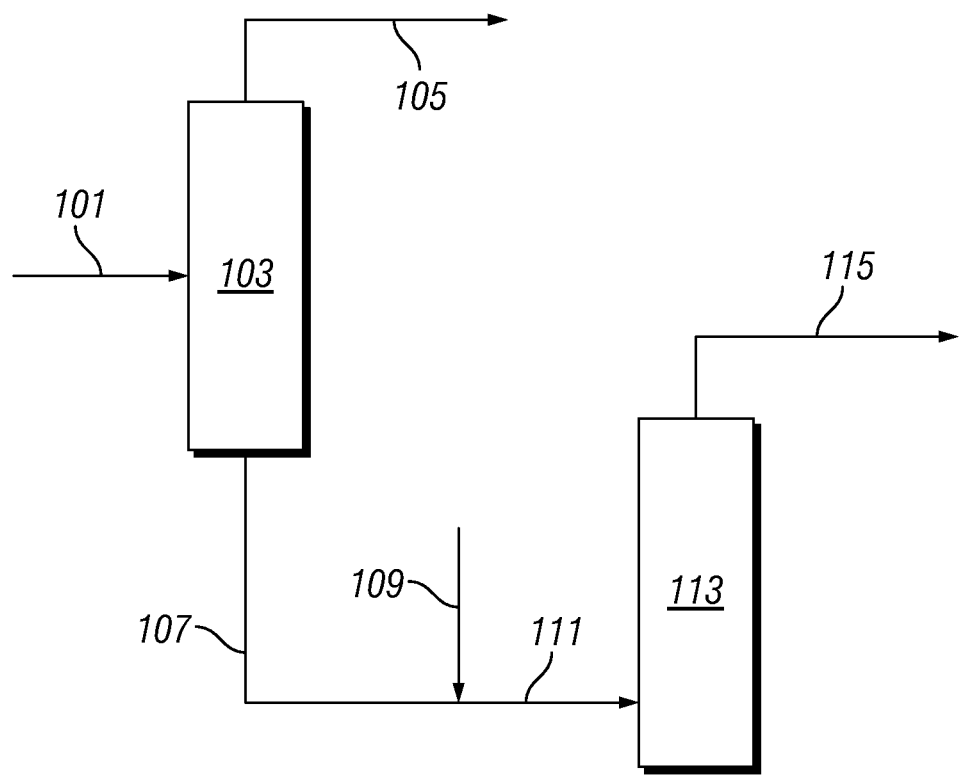
FIG. 1 is a schematic diagram of a system for purifying a crude propane stream according to an embodiment of the present disclosure.

Unless explicitly stated otherwise in defined circumstances, all percentages, parts, ratios, and like amounts used herein are defined by weight.

Further, in this connection, certain features of the process, apparatus, or system according to this disclosure which are, for clarity, described herein in the context of separate embodiments, may also be provided in combination in a single embodiment. Conversely, various features of the process, apparatus, or system according to this disclosure that are, for brevity, described in the context of a single embodiment, may also be provided separately or in any sub-combination.

When describing a range of dimensions, concentrations, pHs, and the like, it is the Applicant's intent to disclose every individual number that such a range could reasonably encompass, for example, every individual number that has at least one more significant figure than in the disclosed end points of the range. As an example, when referring to a pH as between 2 and 3, it is intended to disclose that the pH can be 2, 2.1, 2.2, 2.3, 2.4, 2.5, 2.6, 2.7, 2.8, 2.9, or 3.0, including any subranges or combinations of subranges encompassed in this broader range. Applicant's intent is that these two methods of describing the range are interchangeable. Moreover, when a range of values is disclosed or claimed, Applicant also intends for the disclosure of a range to reflect, and be interchangeable with, disclosing any and all sub-ranges and combinations of sub-ranges encompassed therein. Accordingly, Applicant reserves the right to proviso out or exclude any individual members of any such group, including any sub-ranges or combinations of sub-ranges within the group, or any selection, feature, range, element, or aspect that can be claimed, if for any reason Applicant chooses to claim less than the full measure of the disclosure, for example, to account for a reference that Applicant may be unaware of at the time of the filing of the application. In addition, the ranges set forth herein include their endpoints unless expressly stated otherwise.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. An amount, size, formulation, parameter or other quantity or characteristic is "about" or "approximate" whether or not expressly stated to be such. The term "about" also encompasses amounts that differ due to different equilibrium conditions for a composition resulting from an initial mixture. Whether or not modified by the term "about", the claims include equivalents to the quantities. The term "about" may mean within 10% of the reported numerical value, for example, within 5% of the reported numerical value.

One or more specific embodiments or aspects of the present disclosure are described herein. Crude propane streams, for example from the POSM process, may contain a number of impurities that need to be separated from the propane before the propane is sufficiently pure to be used in other processes or sold to end consumers. For example, crude propane streams may contain impurities such as propylene oxide, acetaldehyde, and/or propylene.

Distillation is a common method of purifying propane streams. However, removing common impurities such as propylene oxide and acetaldehyde from crude propane streams is impractical or infeasible with distillation, because the relative volatilities of acetaldehyde and propane are very close to 1.0. Further, during distillation, acetaldehyde is very likely to polymerize, forming red oil (carbonyl polymer), which is likely to foul the plates and lines of the distillation column.

Scavengers may be added to remove, reduce, or de-activate impurities and unwanted reaction products. For example, an acetaldehyde scavenger may be added to reduce the acetaldehyde content of a propane stream.

In some embodiments, the crude propane stream may contain from about 0.5 wt. % to about 6.0 wt. % propylene oxide, for example about 0.5 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, about 5.0 wt. %, about 5.5 wt. %, about 6.0 wt. %, or any ranges therebetween.

In some embodiments, the crude propane stream may include from about 1 wt. % to about 4 wt. % acetaldehyde, for example about 1.0 wt. %, about 1.5 wt. %, about 2.0 wt. %, about 2.5 wt. %, about 3.0 wt. %, about 3.5 wt. %, about 4.0 wt. %, or any ranges therebetween.

In some embodiments, methods of purifying a crude propane stream are provided. In one embodiment, the method includes: providing a crude propane stream comprising propane, propylene oxide, acetaldehyde, and propylene; contacting a crude propane stream with a Beta zeolite catalyst to reduce the propylene oxide content of the crude propane stream and produce a first treated propane stream; and contacting the first treated propane stream with an acetaldehyde scavenger to reduce the acetaldehyde content of the first treated propane stream and produce a second treated propane stream.

In some embodiments, the crude propane stream may be provided from a C3 splitter of a propylene oxide/styrene monomer process. For example, in some embodiments, the crude propane stream may be derived from an epoxidation of propylene process.

In some embodiments, the crude propane stream is contacted with the zeolite catalyst in a fixed bed reactor. In some embodiments, the first treated propane stream with the acetaldehyde in a fixed bed reactor. In some embodiments, the Beta zeolite catalyst is Zeolyst® CP 7146, Zeolyst® CP 811E-300, Zeolyst® CP 811C-300, or a combination thereof. In some embodiments, the zeolite is selected from a faujasite, a mordenite, a chavbazite, a clinoptilolite, an erionite, a sihealite, a zeolite A, a zeolite L, a zeolite beta, a zeolite X, a zeolite Y, a zeolite HY, a zeolite ZSM-5, a zeolite MCM-22, a zeolite MCM-41, a zeolite UCB-1, and a zeolite ITQ-2. In some embodiments, the acetaldehyde scavenger is an amino alcohol. In some embodiments, the acetaldehyde scavenger is Dorf Ketal™ DA 2604 a solution available from Dorf Ketal™ or Dow AMP-95®, a 2-Amino-2-methyl propanol solution. In some embodiments, the acetaldehyde scavenger may be a carbohydrazide base anti-polymerant for a caustic wash tower, as described in U.S. Pat. Nos. 5,582,808 and 5,160,425, which are both hereby incorporated herein by reference in its entirety. In some embodiments, the acetaldehyde scavenger is a liquid. In some embodiments, the Beta zeolite catalyst or the acetaldehyde scavenger are diluted to minimize mass diffusion effects. In some embodiments, the Beta zeolite catalyst or the acetaldehyde scavenger may be diluted with 120-220 μm mesh silicon carbide. In some embodiments, the crude propane stream is first contacted with the zeolite catalyst to form a propylene-treated stream and then the propylene-treated stream is contacted with an acetaldehyde scavenger in a static mixer to produce a treated propane stream.

In some embodiments, the crude propane stream has a temperature of from about 60° F. to about 200° F., for example about 60° F., about 80° F., about 100° F., about 120° F., about 140° F., about 160° F., about 180° F., about 200° F., and any ranges therebetween. In some embodiments, the crude propane stream has a pressure of from about 250 psig to about 350 psig, for example about 250 psig, about 260 psig, about 270 psig, about 280 psig, about 290 psig, about 300 psig, about 310 psig, about 320 psig, about 330 psig, about 340 psig, about 350 psig, or any ranges therebetween. In some embodiments, the crude propane stream has a pressure of about 300 psig and a temperature of about 100° F.

In some embodiments, the first treated propane stream includes less than 100 ppm of propylene oxide. For example, about 90 ppm, about 80 ppm, about 70 ppm, about 60 ppm, about 50 ppm, about 40 ppm, about 30 ppm, about 20 ppm, about 10 ppm, about 5 ppm, about 1 ppm, or any ranges therebetween. In some embodiments, the first treated propane stream includes less than about 1 wt % acetaldehyde. For example, about 0.1 wt % acetaldehyde, about 0.2 wt % acetaldehyde, about 0.3 wt % acetaldehyde, about 0.4 wt % acetaldehyde, about 0.5 wt % acetaldehyde, about 0.6 wt % acetaldehyde, about 0.7 wt % acetaldehyde, about 0.8 wt % acetaldehyde, about 0.9 wt % acetaldehyde, or any ranges therebetween.

In some embodiments, the second treated propane stream includes less than about 1000 ppm acetaldehyde, for example, about 950 ppm, about 900 ppm, about 800 ppm, about 700 ppm, about 600 ppm, about 500 ppm, about 400 ppm, about 300 ppm, about 200 ppm, about 100 ppm, about 50 ppm, about 10 ppm, about 5 ppm, about 1 ppm, or any ranges therebetween.

In some embodiments, reactors and reactor systems for purifying a crude propane stream are provided. In one embodiment, a reactor for purifying a crude propane stream includes: an acetaldehyde scavenger injection system configured to inject one or more acetaldehyde scavengers into a crude propane stream; a bed reactor having a first inlet configured to receive the crude propane stream and one or more acetaldehyde scavengers, the fixed bed reactor comprising a Beta zeolite configured to contact the crude propane stream, reduce the propylene oxide content of the crude propane stream, and produce a first treated propane stream. The fixed bed reactor may be of any suitable design. For example, the reactor may be of the type described in U.S. Pat. No. 7,279,145, entitled "Multiphase Reactor Design Incorporating Filtration System for Fixed-Bed Catalyst," which is hereby incorporated herein by reference in its entirety, or may be of the type described in U.S. Pat. No. 8,710,274, entitled "Method of Purifying Crude Acetone Stream," which is hereby incorporated herein by reference in its entirety.

In one embodiment, a reactor for purifying a crude propane stream includes: a fixed bed reactor having a first inlet configured to receive a crude propane stream, the crude propane stream comprising propane, propylene oxide, acetaldehyde, and propylene; the fixed bed reactor comprising a Beta zeolite configured to contact the crude propane stream, reduce the propylene oxide content of the crude propane stream, and produce a first treated propane stream; and a static mixer configured to mix at least a portion of the one or more of the crude propane stream and the first treated propane stream with an acetaldehyde scavenger to reduce the acetaldehyde content of the first treated propane stream, and produce a second treated propane stream.

In some embodiments, propane production systems are provided which can comprise: a first system configured to produce a first hydrocarbon stream comprising C3 hydrocarbons; a distillation column configured to separate propylene and propane and produce a crude propane stream; and one or more reactors configured to purify the crude propane stream. In some embodiments, the one or more reactors include a fixed bed zeolite reactor. In some embodiments, the one or more reactors include a water wash.

In some embodiments, methods of purifying a crude propane stream are provided. In one embodiment, a method of purifying a crude propane stream includes: providing a crude propane stream comprising propane, propylene oxide, acetaldehyde, and propylene; and passing the crude propane stream through a water wash system to provide a treated propane stream having a lower propylene oxide content, a lower acetaldehyde content, or both; wherein the water wash system comprises treating water in a water wash column with at least 15 theoretical stages.

In some embodiments, the weight ratio of treating water to the crude propane stream is from about 1 to about 6, for example about 1, about 1.5, about 2, about 2.5, about 3, about 3.5, about 4, about 4.5, about 5, about 5.5, about 6, or any ranges therebetween. In some embodiments, the treating water has a pH of from about 6.8 to 7.6, for example about 6.8, about 6.9, about 7.0, about 7.1, about 7.2, about 7.3, about 7.4, about 7.5, about 7.6, or any ranges therebetween.

In some embodiments, the treating water may be fresh water. In some embodiments, the treating water may be recycled water from another system. For example, in some embodiments, the treating water may be water condensed from a reboiler. In some embodiments, a propane production system may include a reboiler configured to produce a water vapor stream, and a condenser configured to condense a portion of the water vapor stream to form a liquid treating water stream. The treating water stream may then be used in a water wash system to purify a crude propane stream.

In some embodiments, the treating water may be caustic waste water. For example, in some embodiments, the treating water may be deep well waste water, such as waste water from natural gas fracking.

ILLUSTRATED EMBODIMENTS

FIG. 1 shows a schematic diagram of a system for purifying a crude propane stream. In this embodiment, a mixed C3 stream 101 is provided to a C3 splitter 103. For example, this mixed C3 stream 101 may be provided from a propylene oxide/styrene monomer process. The C3 splitter produces a propylene stream 105 and a crude propane stream 107. An acetaldehyde scavenger stream 109 is added to the crude propane stream 107 to provide an acetaldehyde-treated stream 111. The acetaldehyde-treated stream 111 is then provided to a reactor 113 which includes a Beta zeolite catalyst to reduce the propylene oxide content and produce a treated propane stream 115. The acetaldehyde scavenger stream 109 is added to the crude propane stream 107 upstream of the reactor 113. In other embodiments, the acetaldehyde scavenger stream may be added to the treated propane stream, or may be added downstream of the reactor.

Figure 2:
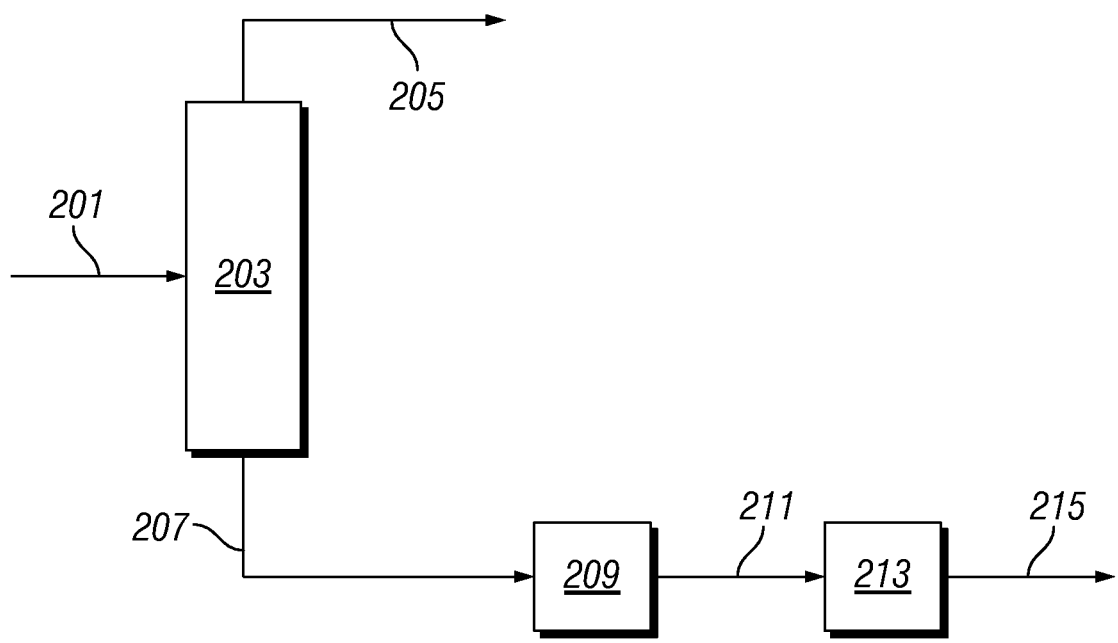
FIG. 2 is a schematic diagram of a system for purifying a crude propane stream according to another embodiment of the present disclosure.

FIG. 2 shows a schematic diagram of a system for purifying a crude propane stream. In this embodiment, a mixed C3 stream 201 is provided to a C3 splitter 203. For example, this mixed C3 stream may be provided from a propylene oxide/styrene monomer process. The C3 splitter produces a propylene stream 205 and a crude propane stream 207. The crude propane stream 207 is provided to a reactor 209 which includes a Beta zeolite catalyst to reduce the propylene oxide content and produce a first treated propane stream 211. The first treated propane stream 211 is then provided to a static mixer 213, where the stream is contacted with an acetaldehyde scavenger to reduce the acetaldehyde content of the first treated propane stream 211 and produce a second treated propane stream 215.

Figure 3:
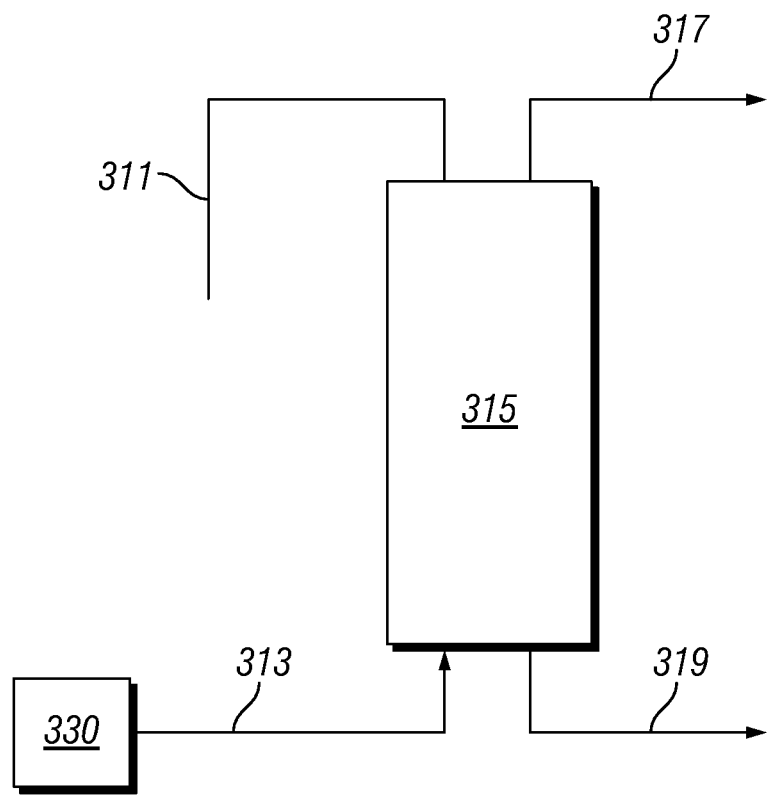
FIG. 3 is a schematic diagram of a water wash system for purifying a crude propane stream according to an embodiment of the present disclosure.

FIG. 3 shows a schematic diagram of a water wash system for purifying a crude propane stream. A liquid water stream 311 and a crude propane stream 313 are provided to a water wash system 315 with at least 15 theoretical stages. In the water wash system 315, the treating water contacts the propane stream, to reduce the propylene oxide content and/or acetaldehyde content of the crude propane stream, and producing a treated propane stream 317 and a water purge stream 319. The liquid water stream 311 may be provided from any suitable source. The crude propane stream 313 may be provided from any source that produces a crude propane stream. For example, as shown in this figure, the crude propane stream 313 is obtained from a propylene oxide/styrene monomer (POSM) manufacturing process 330.

EXAMPLES

Non-limiting embodiments of the present disclosure may be more readily understood by reference to the examples described below.

Example 1: Pilot-Scale Water Wash Testing

Figure 4:
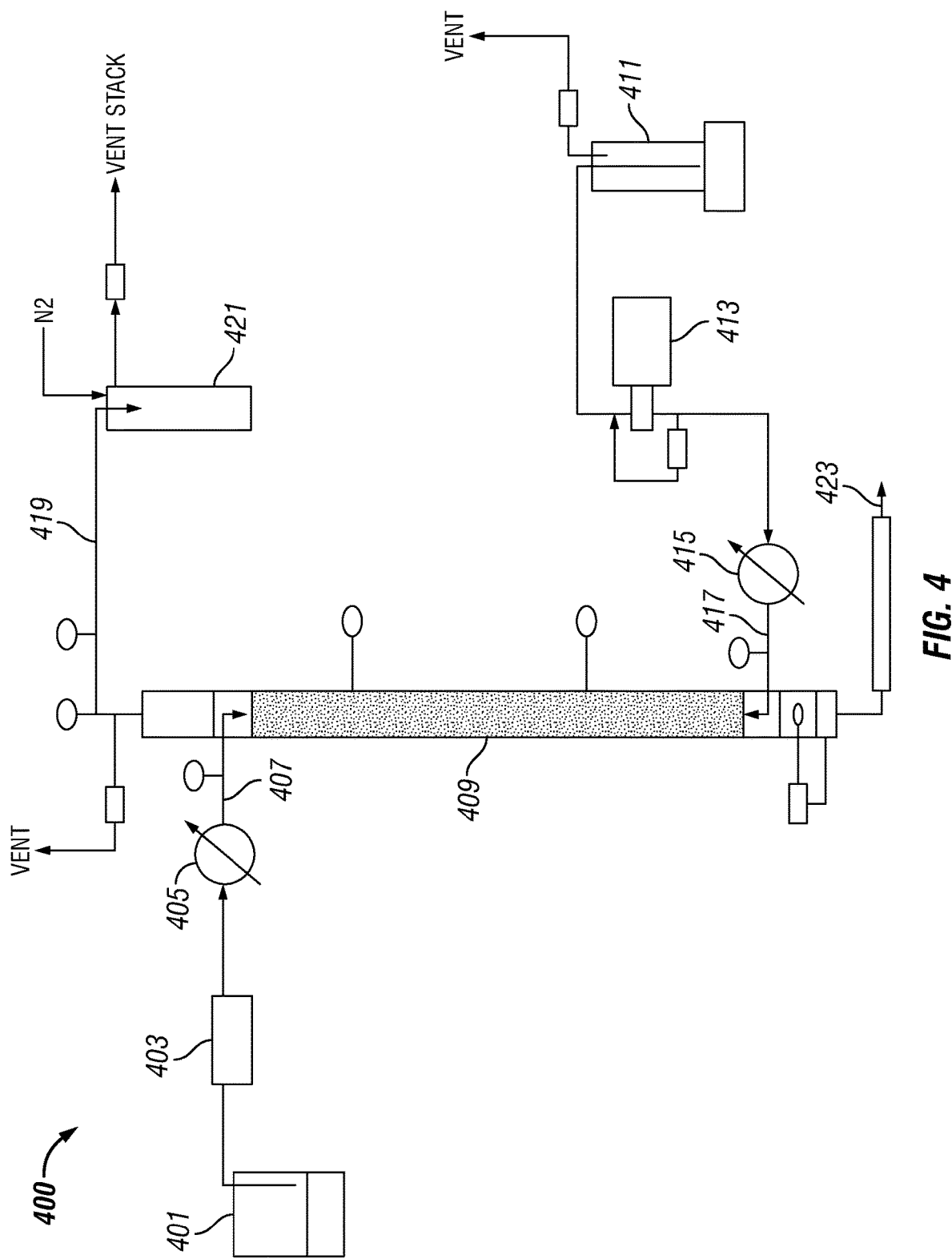
FIG. 4 is a schematic illustration of a water wash system used in pilot-scale experiments according to the present disclosure.

Several pilot-scale experiments were performed to evaluate the effectiveness of water washing at removing propylene oxide and acetaldehyde from a crude propane stream. A schematic illustration of the system used in these experiments is shown in FIG. 4. A water feed 401 was pumped by water pump 403 at a rate of 3.37 mL/min and fed to a heater 405 to produce a heated water stream 407. This heated water stream 407 was then fed to the top of a water wash column 409. The water wash column 409 was one inch in diameter and sixty inches in length, and was operated at a pressure of about 300 psig.

A cylinder 411 filled with a crude propane stream was provided, and pumped with a C3 pump 413 to a second heater 415, to form a heated crude propane stream 417. A purified propane stream 419 was fed to a recovery vessel 421, and a stream of used treating water 423 was treated as waste. Thirteen experiments were performed, and in each experiment, the crude propane stream contained about 4 wt. % acetaldehyde and about 3 wt. % propylene oxide. The experimental conditions used are shown in Table 1 below:

TABLE 1

| Experiment No. | Water pH | Water:Propane Ratio | Temperature (° F.) | Wt. % Acetaldehyde in Treated Propane Stream | Wt. % Propylene Oxide in Treated Propane Stream |
|---|---|---|---|---|---|
| 1 | 6.8 | 4:1 | 120 | 0.068 | 0.25 |
| 2 | 6.8 | 2:1 | 100 | 0.077 | 1.11 |
| 3 | 7.5 | 6:1 | 120 | 0 | 0.12 |
| 4 | 7.5 | 2:1 | 100 | 0.069 | 0.836 |
| 5 | 7 | 6:1 | 100 | 0.07 | 0.092 |
| 6 | 6.8 | 2:1 | 120 | 0.0719 | 0.77 |
| 7 | 7.5 | 6:1 | 100 | 0.044 | 0.092 |
| 8 | 7 | 6:1 | 120 | 0.069 | 0.23 |
| 9 | 7 | 2:1 | 120 | 0.076 | 0.81 |
| 10 | 6.8 | 4:1 | 100 | 0.078 | 0.51 |
| 11 | 7 | 2:1 | 100 | 0.069 | 0.58 |
| 12 | 7.5 | 2:1 | 120 | 0.068 | 0.72 |
| 13 | 7.5 | 3:1 | 110 | 0.07 | 0.22 |

As can be seen from these experimental results, the water:propane ratio and the pH of the treatment water had the greatest effect on the wt. % of acetaldehyde and propylene oxide remaining in the treated propane stream. Specifically, lower concentrations of acetaldehyde and propylene oxide are achieved with higher water:propane ratios and higher treating water pH. Conversely, temperature did not appear to affect the removal of acetaldehyde or propylene oxide.

Example 2: Pilot-Scale Beta Zeolite Testing

Figure 5:
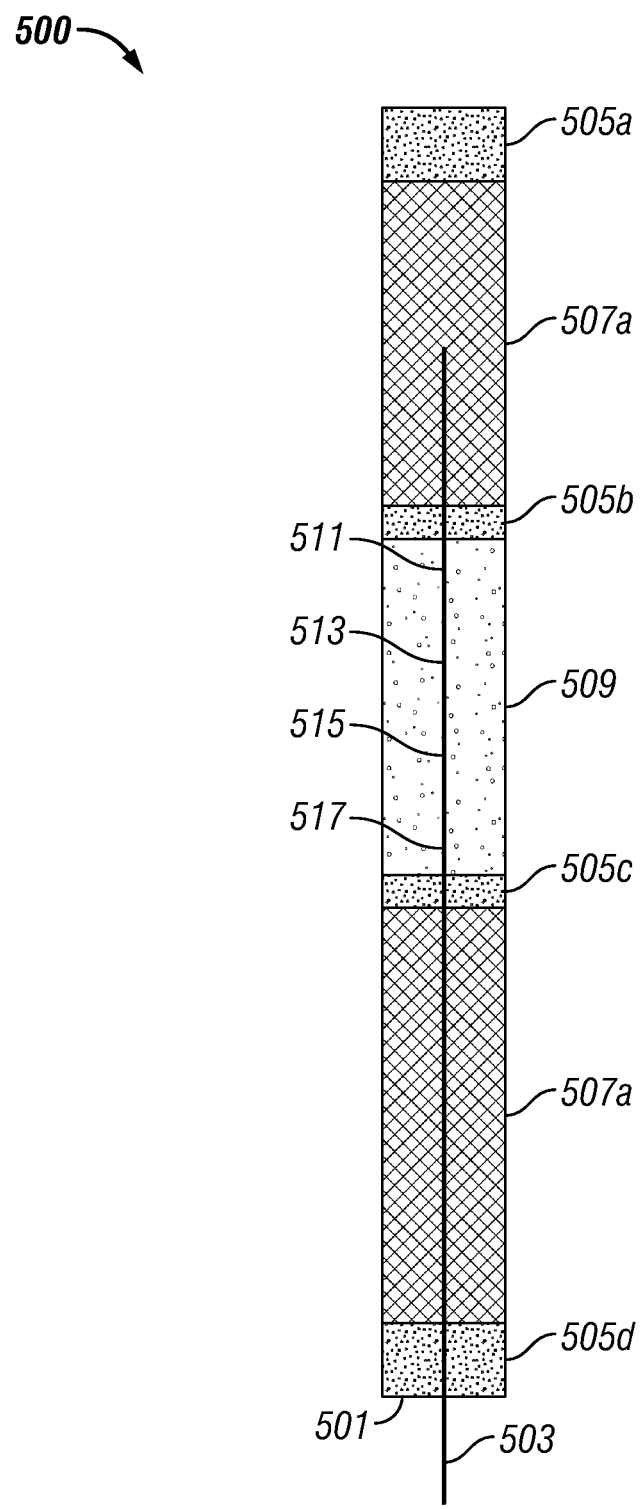
FIG. 5 is a schematic illustration of the fixed bed zeolite reactor used in pilot-scale experiments according to the present disclosure.

Several experiments were conducted using a lab-scale fixed bed reactor with an internal diameter of 25.4 mm. Several catalysts were used, diluted with silicon carbide to reduce mass diffusion effects. The specific orientation of the fixed bed reactor is shown in FIG. 5. The fixed bed reactor 500 includes a bottom end 501 configured to accept a crude propane stream 503. The crude propane stream 503 contained from about 2 wt. % to about 4 wt. % propylene oxide and from about 1.5 wt. % to about 2 wt. % acetaldehyde, and an aldehyde scavenger was added to the crude propane stream at a temperature of about 180° F. and a molar ratio equivalent of about 1:1 scavenger to acetaldehyde. The fixed bed reactor included layers of glass wool 505a, 505b, 505c, and 505d, layers of silicon carbide 507a and 507b. The fixed bed reactor further included a single layer of catalyst 509 diluted with 120-220 μm mesh silicon carbide. The fixed bed reactor included four outlets: 511, 513, 515, and 517 to collect the purified propane stream.

Using this setup, several experimental tests were performed, using Zeolyst® CP 7146 catalyst and Dorf Ketal™ DA 2604 acetaldehyde scavenger. Experiments were performed at ambient temperature, 104° F., and 200° F., at a temperature of 290 psi and a residence time of about 1 hour across the catalyst bed. Using an acetaldehyde scavenger at these conditions, acetaldehyde concentrations in the treated propane stream were reduced to less than 1000 ppm, and propylene oxide concentrations were reduced to less than 1 wt. %. It was also observed that more propylene oxide and acetaldehyde were removed at higher temperatures. While not intending to be bound by theory, it is believed that this may be due to an improved catalyst life at higher temperatures.

Figure 6:
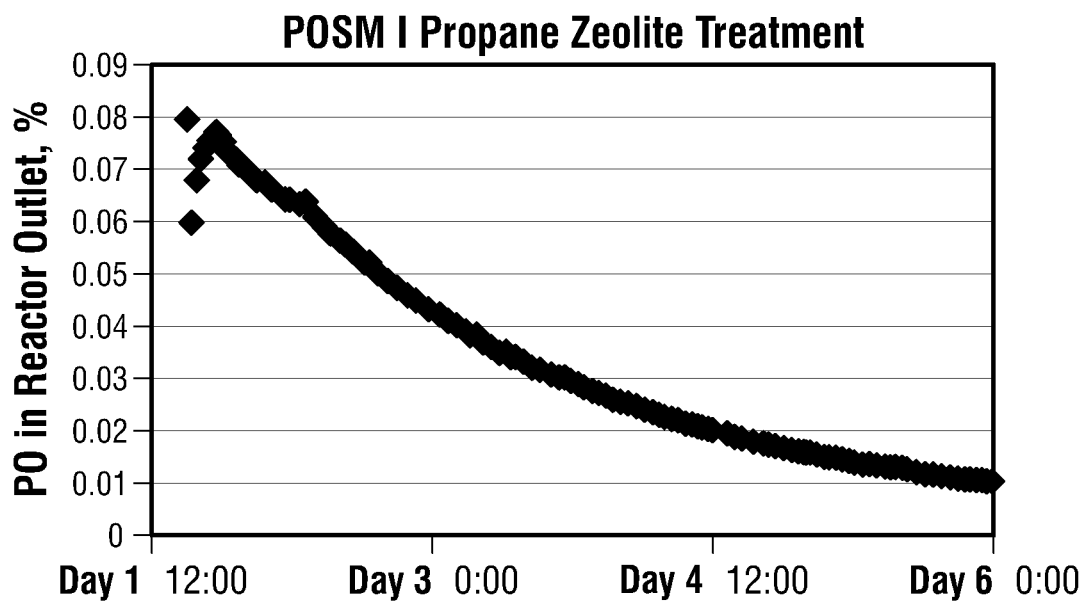
FIG. 6 is a graph of the concentration of propylene oxide in the outlet of a fixed bed zeolite reactor used in pilot-scale experiments according to the present disclosure.
Figure 7:
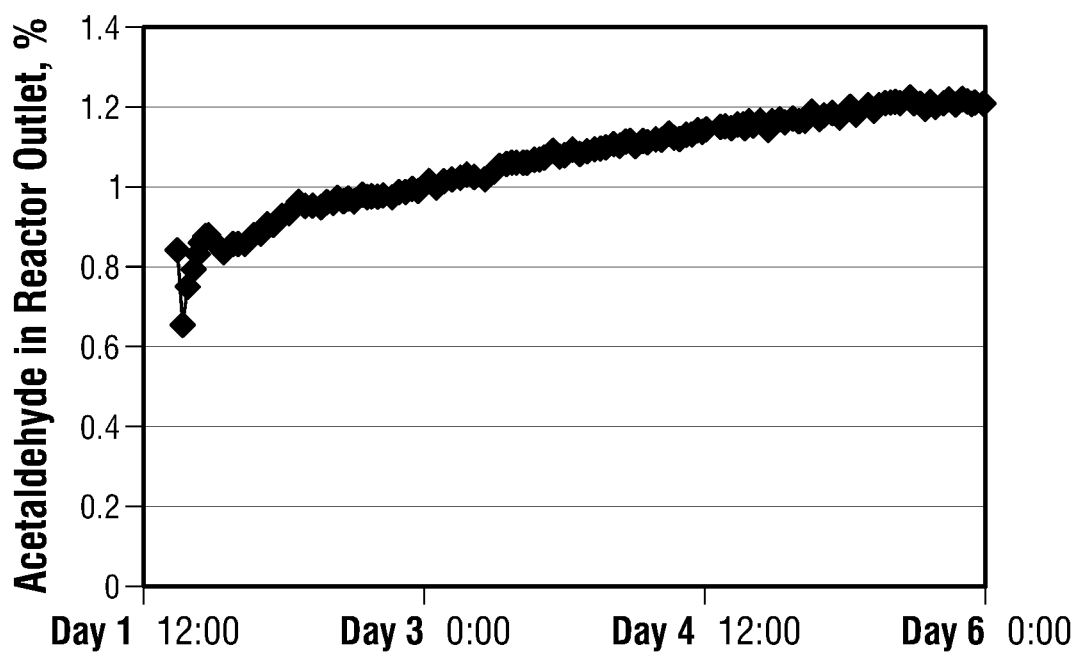
FIG. 7 is a graph of the concentration of acetaldehyde in the outlet of a fixed bed zeolite reactor used in pilot-scale experiments according to the present disclosure.

Several experiments were performed omitting the acetaldehyde scavenger, with a crude propane stream containing 4 wt. % acetaldehyde and 3.5 wt. % propylene oxide. As can be seen from FIG. 6, the concentration of propylene oxide in the reactor outlet decreased steadily throughout the length of the experiment, and was less than 0.1 wt % throughout. In contrast, as can be seen from FIG. 7, without the use of an acetaldehyde scavenger, the concentration of acetaldehyde in the reactor outlet was at an unacceptable concentration of from 0.6 wt. % to 1.3 wt. % throughout the experiment.

Once a Dorf Ketal™ DA 2604 acetaldehyde scavenger was added, the acetaldehyde concentration was reduced to less than 1000 ppm, as reported above. However, it was discovered that, in spite of the reduction in acetaldehyde, there was still a presence of red oil (carbonyl polymer) resulting from the polymerization of acetaldehyde. The red oil caused some line plugging during the experiment.

The present disclosure is described above with reference to numerous aspects and embodiments, and specific examples. Equivalents and certain variations of the disclosed embodiments will suggest themselves to those skilled in the art in light of the above detailed description, which are within the intended scope of the appended claims.

What is claimed is:

1. A reactor for purifying a crude propane stream, the reactor comprising:
   a fixed bed reactor having a crude propane stream inlet, the crude propane stream comprising propane, propylene oxide, acetaldehyde, and propylene;
   the fixed bed reactor comprising a Beta zeolite configured to contact the crude propane stream, reduce the propylene oxide content of the crude propane stream, and produce a first treated propane stream; and
   an acetaldehyde scavenger system configured to contact one or more of the crude propane stream and the first treated propane stream with one or more acetaldehyde scavengers under conditions sufficient to reduce the acetaldehyde content of the one or more of the crude propane stream and the first treated propane stream.

2. The reactor system of claim 1, wherein the acetaldehyde scavenger system comprises a static mixer configured to mix at least a portion of the one or more of the crude propane stream and the first treated propane stream with an acetaldehyde scavenger to produce a second treated propane stream.

3. A propane production system comprising:
   a first system configured to produce a first hydrocarbon stream comprising C3 hydrocarbons;
   a distillation column configured to separate propylene and propane and produce a crude propane stream;
   the reactor of claim 1 configured to purify the crude propane stream.

* * * * *